United States Patent
Rundo et al.

(10) Patent No.: US 10,362,985 B2
(45) Date of Patent: Jul. 30, 2019

(54) METHOD AND SYSTEM FOR ANALYZING SKIN LESIONS

(71) Applicant: STMicroelectronics S.r.l., Agrate Brianza (IT)

(72) Inventors: Francesco Rundo, Gravina di Catania (IT); Giuseppe Luigi Banna, Catania (IT)

(73) Assignee: STMicroelectronics S.r.l., Agrate Brianza (MB) (IT)

( * ) Notice: Subject to any disclaimer, the term of this patent is extended or adjusted under 35 U.S.C. 154(b) by 209 days.

(21) Appl. No.: 15/607,178

(22) Filed: May 26, 2017

(65) Prior Publication Data

US 2018/0146912 A1 May 31, 2018

(30) Foreign Application Priority Data

Nov. 29, 2016 (IT) .................. 102016000121060

(51) Int. Cl.
  *G06T 5/00* (2006.01)
  *A61B 5/00* (2006.01)
  (Continued)

(52) U.S. Cl.
  CPC ............ *A61B 5/444* (2013.01); *A61B 5/0073* (2013.01); *A61B 5/7264* (2013.01);
  (Continued)

(58) Field of Classification Search
  USPC ....................................................... 382/128
  See application file for complete search history.

(56) References Cited

U.S. PATENT DOCUMENTS 6,081,612 A * 6/2000 Gutkowicz-Krusin ..................... A61B 5/0071
  382/128
8,543,519 B2 * 9/2013 Guyon .................. G06T 7/0012
  706/12

(Continued)

OTHER PUBLICATIONS

Duff, C.G. et al., "A 6 year Prospective Anaylysis of the Diagnosis of Malignant Melanoma in a Pigmented-Lesion Clinic: Even the Experts Miss Malignant Melanomas, but Not Often," British Journal of Plastic Surgery, vol. 54, Issue 4, Jun. 2001, pp. 317-321.

(Continued)

*Primary Examiner* — Ishrat I Sherali
(74) *Attorney, Agent, or Firm* — Slater Matsil, LLP (57) ABSTRACT

A method can be used for analyzing digital images of skin lesions. The images include pixels distributed over a lesion area. Sets of values including a first discrimination value indicative of a weighted average of the image pixels with weighing at the border of the lesion, a second discrimination value indicative of skewness and kurtosis of the distribution of the image pixels, a third discrimination value indicative of the ratio of symmetry and gray-level power of the distribution of the image pixels and calculated. A total additive score of the values in the sets of values is provided and compared with a total score threshold. The first, second and third discrimination values are compared with respective first, second and third discrimination threshold values. An output classification for the image analyzed is provided as a function of the results of the comparing.

20 Claims, 3 Drawing Sheets

(51) Int. Cl.
*G06T 7/00* (2017.01)
*A61B 5/103* (2006.01)
*A61B 5/107* (2006.01)

(52) U.S. Cl.
CPC .......... *G06T 7/0012* (2013.01); *A61B 5/1032* (2013.01); *A61B 5/1072* (2013.01); *G01N 2800/20* (2013.01); *G06T 2207/30088* (2013.01); *G06T 2207/30096* (2013.01)

(56) References Cited

U.S. PATENT DOCUMENTS

| | | | | |
|---|---|---|---|---|
| 8,837,832 | B2* | 9/2014 | Kislal | G06T 7/0012 |
| | | | | 382/182 |
| 10,182,757 | B2* | 1/2019 | Gareau | A61B 5/6898 |
| 2004/0267102 | A1* | 12/2004 | Skladnev | A61B 5/442 |
| | | | | 600/315 |
| 2008/0214907 | A1* | 9/2008 | Gutkowicz-Krusin | |
| | | | | A61B 5/0059 |
| | | | | 600/306 |
| 2011/0286643 | A1 | 11/2011 | Kislal | |
| 2015/0025343 | A1* | 1/2015 | Gareau | A61B 5/6898 |
| | | | | 600/328 |
| 2018/0122065 | A1* | 5/2018 | Abedini | G06T 7/0012 |
| 2018/0122076 | A1* | 5/2018 | Abedini | A61B 5/6898 |

OTHER PUBLICATIONS

"Melanoma," Linee Guida, AIOM, Ed. 15, 2015, pp. 9.

Sathiya, S.B. et al., "A Survey on Recent Computer-Aided Diagnosis of Melanoma," 2014 International Conference on Control, Instrumentation, Communication and Computational Technologies (ICCICCT), Jul. 10-11, 2014, pp. 1387-1392.

Iyatomi, H., et al., "Parameterization of Dermoscopic Findings for the Internet-based Melanoma Screening System", IEEE Symposium on Computational Intelligence in Image and Signal Processing (CIISP 2007), pp. 189-193.

Garnavi, R., "Computer-Aided Diagnosis of Melanoma Using Border- and Wavelet-Based Texture Analysis", IEEE Transactions on Information Technology in Biomedicine, vol. 16, No. 6, Nov. 2012, pp. 1239-1252.

Farooq, M., et al., "Automatic Lesion Detection System (ALDS) for Skin Cancer Classification Using SVM and Neural Classifiers", 2016 IEEE 16th International Conference on Bioinformatics and Bioengineering, pp. 301-308.

* cited by examiner

METHOD AND SYSTEM FOR ANALYZING SKIN LESIONS

CROSS-REFERENCE TO RELATED APPLICATIONS

This application claims priority to Italian Patent Application No. 102016000121060, filed on Nov. 29, 2016, which application is hereby incorporated herein by reference.

TECHNICAL FIELD

Embodiments of the invention relate to a method of analyzing skin lesions, a corresponding system, an instrument and a computer program product.

BACKGROUND

The ability of analyzing skin lesions in order to differentiate malignant lesions (cancer or pre-cancer condition) over suspect nevus or benign ones may play a significant role in healthcare-based applications.

Currently, physicians such as oncologists and/or dermatologists may provide a subjective analysis of a nevus with heuristic rules such as, e.g., ABCDE (Asymmetry, Borders, Colors, Diameter, Evolving) to describe a nevus as benign or suspect or malignant. Also, physicians may perform a careful examination of, e.g., nevus by means of dermoscopy, with the personal experience of the physician playing a key role in the evaluation.

Clinical diagnosis of melanoma is thus regarded as generally difficult see, e.g., AIOM Linee Guida (Guidelines) "Melanoma" Ed. 2015, p. 9 (available at www.aiom.it) or C. G. Duff, et al.: "A 6 year prospective analysis of the diagnosis of malignant melanoma in pigmented-lesion clinic: even the experts miss malignant melanoma, but not often." Br J Plas Surg 2001; 54:317-321, with diagnosis directly influenced by the practitioner's experience with a sensitivity between 50 and 85%.

The possibility of reducing the impact of the "human factor", e.g., the heuristic experience of the physician by providing some sort of technical assistance to the medical diagnosis has been investigated to some extent.

For instance, using image features to differentiate malignant skin lesion from atypical/suspect ones has been proposed.

While somehow related to the ABCDE rule, certain techniques may use image features to perform analysis in manner which basically differs from the ABCDE rule. Also, certain proposed procedures perform semi-automatic classification of nevus based on joined clinical/algorithm results and/or propose a nevus classification based on texture analysis of nevus dermoscopy. Certain procedures use a multi-classifier approach based on shape geometry of the nevus as well as a subset of image features (physiological and dermatological.

The related techniques may require fairly extensive hardware (fiberscope, photo-acoustic hardware, various devices for image analysis in the frequency domain, etc. . . . ) and may use statistical recursive CPU-consuming algorithms based on clustering (K-means) or learning (SOM, Artificial Neural Networks—ANN's).

A general survey of recent developments in that area is provided, e.g., in S. Binu Sathiya, et al.: "A survey on recent computer-aided diagnosis of Melanoma"—2014 International Conference on Control, Instrumentation, Communication and Computational Technologies (ICCICCT), Kumaracoil, Thuckalay Tamilnadu Kanyakumari District, India, pp. 1387-1392.

Specifically, various solutions proposed in the literature may be exposed to one or more of the following drawbacks:
  a training-set or CPU intensive/consuming ANN learning may be required;
  possible "over-fitting", training set configuration, centroids of clustering and/or segmentation due to hair in the nevus dermoscopy may represent issues of concern;
  the results may exhibit low sensitivity and accuracy in, e.g., nevus classification, especially for suspected skin lesions which are neither benign nor melanoma;
  in most instances, the outcome may be a "binary" result: melanoma or NOT melanoma, which may be unsatisfactory, e.g., for nevus which, while not benign may require monitoring as it cannot be classified as "melanoma" skin lesion yet;
  information about nevus does not include information about future evolution, e.g., a score of possible evolution of analyzed nevus into malignant skin lesion such as melanoma;
  follow-up of the analyzed skin lesion is not provided or, if provided, is affected by issues of image registration, that is synchronizing two sets of diagnostic images taken at distinct times.

For instance, comparing in an accurate manner, e.g., CT scan images or MRI images may require "putting in register" (that is aligning) the images by making it possible to superpose the various slices in order to permit, e.g., an automated algorithm-based comparison.

Similarly, conventional methods of analyzing dermoscopic images may require that, e.g., nevus images taken at different times should be adapted to be superposed or have registration point making it possible to superpose at least the ROI (Region Of Interest) of the images so that results obtained by an analysis algorithm may be compared.

SUMMARY

The description relates to classifying skin lesions. One or more embodiments may be used in support to diagnostic activity in the medical field.

One or more embodiments may also relate to a corresponding system, a corresponding instrument (optionally including a dermoscopic camera to provide digital images of skin lesions to be analyzed), and a computer program product loadable in the memory of at least one processing device and including software code portions for executing the steps of the method when the product is run on at least one computer. As used herein, reference to such a computer program product is understood as being equivalent to reference to a computer-readable medium containing instructions for controlling the processing system in order to co-ordinate implementation of the method according to one or more embodiments. Reference to "at least one processor device" is intended to highlight the possibility for one or more embodiments to be implemented in modular and/or distributed form.

The claims are an integral part of the technical disclosure of embodiments as provided herein.

One or more embodiments may permit to discriminate skin lesions in, e.g., three different areas: benign, suspect (e.g., dysplastic nevus) and malignant, with an associated probability of evolution of the skin lesion to cancer.

For instance, one or more embodiments may provide an automatic system for analyzing skin lesions (e.g., nevus)

with the capability of supporting diagnosis by a physician with classifications such as, e.g.:

benign nevus (nevus which shows low probability of malignant evolution to cancer such as melanoma and related differentiations);

suspect (atypical)/dysplastic nevus (nevus which shows medium probability of malignant evolution to cancer so that a specific follow-up may be recommended);

malignant nevus (nevus which shows very high probability of malignant evolution to cancer, that is with a high likelihood to result, e.g., in melanoma).

One or more embodiments may provide a pipeline which may provide, e.g., information which may suggest follow-up of the nevus, providing a specific measure of nevus evolution (based on Fx features comparison) with respect to previous analysis.

One or more embodiments may identify nevus characteristics with high accuracy via an ad-hoc function, with the possibility of avoiding the use of neural networks which may possibly require an extensive preliminary learning configuration.

One or more embodiments may jointly rely on different functions:

a first one (e.g., $F_{12}$) to implement A (Asymmetry), B(Borders), C(Color), D(Diameter) in support of oncologist to identify a suspected skin lesion (the so-called ABCDE method);

a second one (e.g., $F_{17}$) providing a specific and accurate average measure of asymmetry, borders irregularity of an analyzed nevus ("A", "B", of the ABCDE rule) based on customized/ad-hoc measure of kurtosis and skewness (classical imaging indicators) of the analyzed lesion; and a third one (e.g., $F_{22}$) providing a weighted average measure of ratio between nevus symmetry and "gray-level power" wherein the denominator of a proposed feature may include grey intensity (e.g., as an add-on to the classical ABCDE method).

In one or more embodiments such classification may include classes such as, e.g.:

nevus with no irregularities, with very low/low probability of evolution to malignant skin lesion (P=<1%);

nevus with some irregularities, having medium probability of evolution to malignant skin lesion (P=~30/40%);

nevus (e.g., as Clark Nevus) with "some-plus" irregularities, having "medium-plus" probability of evolution to malignant skin lesion (P=45/65%);

nevus with several irregularities, having high probability of evolution to malignant skin lesion (P=90/100%);

nevus with "several-plus" irregularities, with a "high-plus" probability of evolution to malignant skin lesion—melanoma in progress (P=~100%).

One or more embodiments may exhibit one or more of the following features/advantages:

real-time segmentation (and hair removal) of nevus dermoscopy;

"fuzzy" analysis with computation of probability of malignant evolution;

ad-hoc analysis of, e.g., a nevus image by means of ad-hoc feature analysis in cross-cooperation with the physician who will provide the diagnosis;

a numerical vector may be provided which can be used to validate evolution of nevus within the framework of a suggested follow-up without issues of image registration (registration invariance);

resorting to neural network or clustering algorithms requiring preliminary learning e/o adaptive clusters configuration may be avoided, thus dispensing with issues of over-fitting, initial condition model dependency, and so on;

registration constraints are overcome insofar as the method of one or more embodiments and the features used therein may not be affected, e.g., by a different orientation, angle of view, roto-translation of a lesion subject to analysis within a dermoscopic image;

one or more embodiments may be easily implemented, e.g., as firmware running in a System-on-Chip (SoC) layout without additional hardware required.

BRIEF DESCRIPTION OF THE DRAWINGS

One or more embodiments will now be described, by way of example only, with reference to the annexed figures, wherein.

DETAILED DESCRIPTION OF ILLUSTRATIVE EMBODIMENTS

In the ensuing description, one or more specific details are illustrated, aimed at providing an in-depth understanding of examples of embodiments of this description. The embodiments may be obtained without one or more of the specific details, or with other methods, components, materials, etc. In other cases, known structures, materials, or operations are not illustrated or described in detail so that certain aspects of embodiments will not be obscured.

Reference to "an embodiment" or "one embodiment" in the framework of the present description is intended to indicate that a particular configuration, structure, or characteristic described in relation to the embodiment is comprised in at least one embodiment. Hence, phrases such as "in an embodiment" or "in one embodiment" that may be present in one or more points of the present description do not necessarily refer to one and the same embodiment. Moreover, particular conformations, structures, or characteristics may be combined in any adequate way in one or more embodiments.

The references used herein are provided merely for convenience and hence do not define the extent of protection or the scope of the embodiments.

Figure 1:
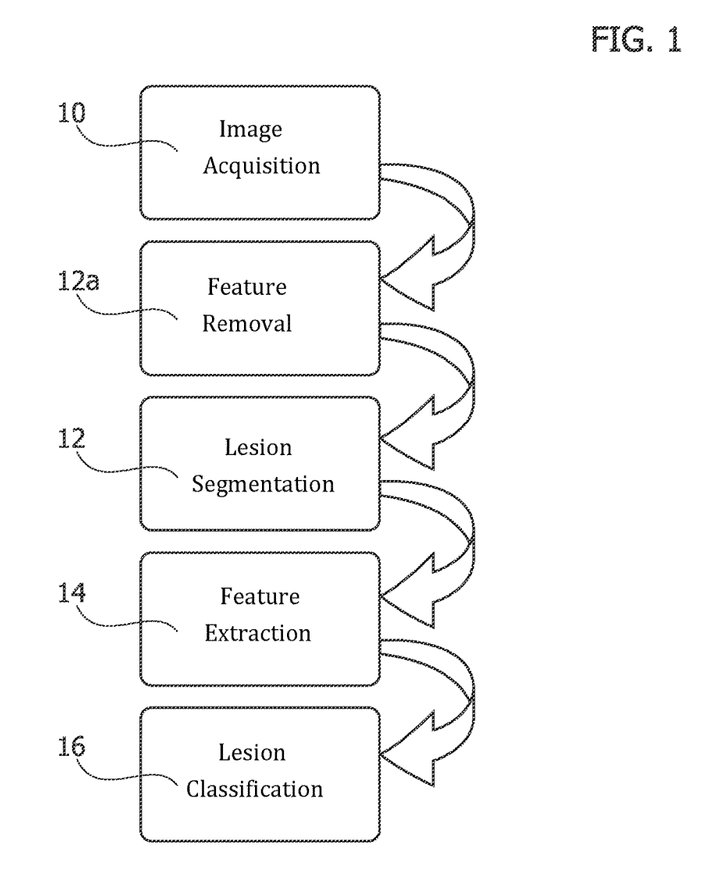
FIG. 1 is generally exemplary of a procedure for classifying (discriminating) skin lesions.

By way of general reference, FIG. 1 is exemplary of a procedure for classifying (discriminating) skin lesions such as, e.g., nevus, including steps such as:

10: acquisition of at least one image of a skin area exhibiting a lesion to be evaluated;

12: lesion segmentation with possible removal 12a of undesired visual features (e.g., hair) which may adversely affect the evaluation process;

14: feature extraction;

16: lesion classification.

Figure 2:
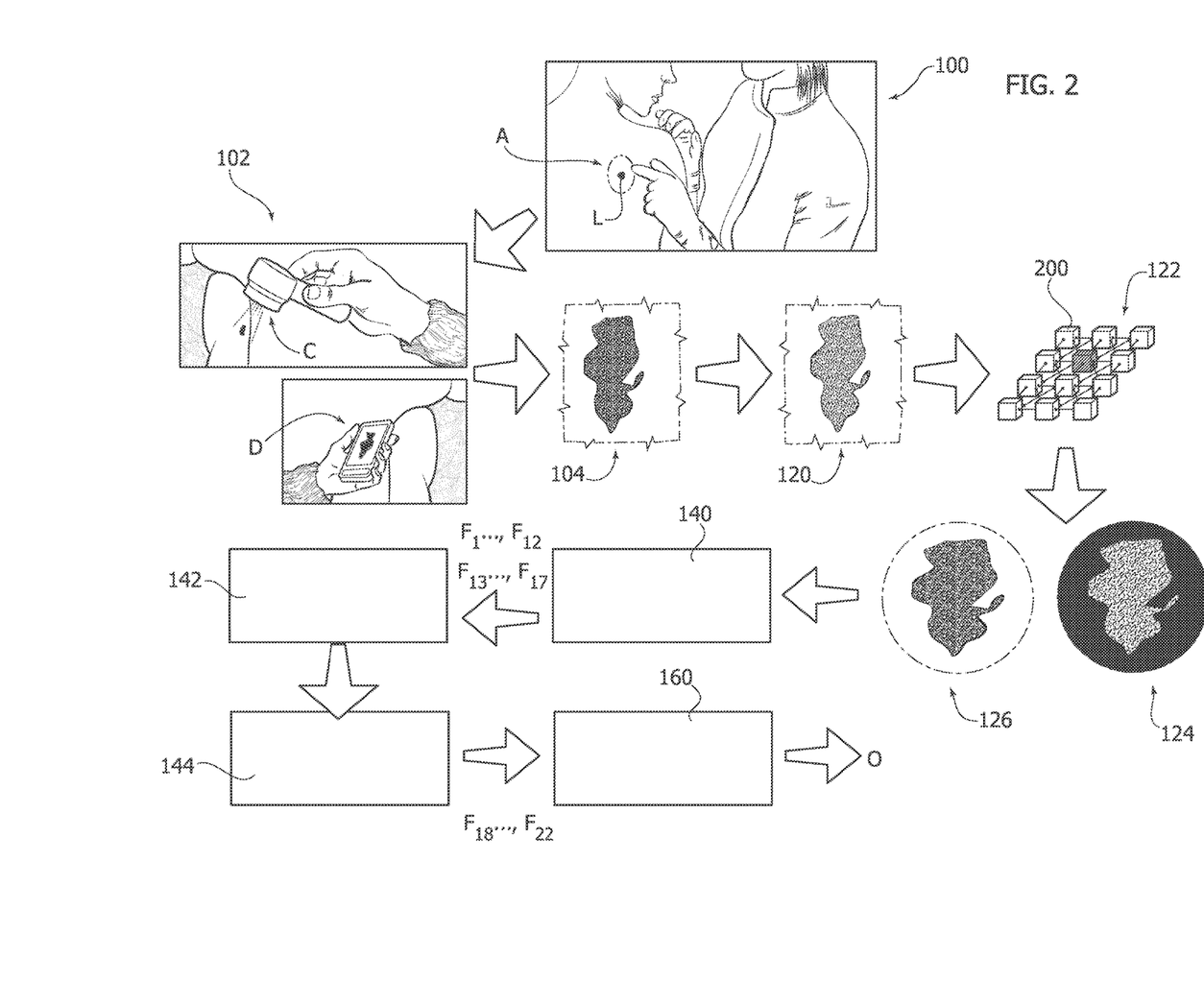
FIG. 2, is an exemplary representation of one or more embodiments.

FIG. 2 is a more detailed exemplary representation of a procedure underlying one or more embodiments.

Such a procedure may include, e.g., a step too leading to identification (e.g., by a physician) of an area A of a patient's skin having a lesion L to be evaluated with possible activity by the physician including one or more steps 102 leading to acquisition of at least one image 104 of the skin area A with the lesion L to be evaluated.

In performing that activity the physician may avail himself or herself of a dermoscopy instrument D including a system as exemplified in the following, optionally in combination with a dermoscopic camera C adapted to provide digital (e.g., color) images 104 of skin lesions to be analyzed.

The procedure as exemplified in FIG. 1 may then include:

a first set of processing steps 120, 122, 124, 126 leading to segmentation of the lesion (image) with possible removal of undesired visual features;

a second set of processing steps, including, e.g., feature processing 140, edge detection 142 and further feature processing 144; and evaluation of the results of previous processing, e.g., via fuzzy-like if-then-else evaluation at 160 leading to providing an outcome O in the form of information in support of the physician's diagnostic activity (e.g., "Nevus with . . . Probability of melanoma evolution . . . ").

In one or more embodiments, such information may be include a so-called F_vector of a number of features, e.g., [Fi|i=1, . . . , 22] conveying respective items of information in support of diagnosis.

Figure 3:
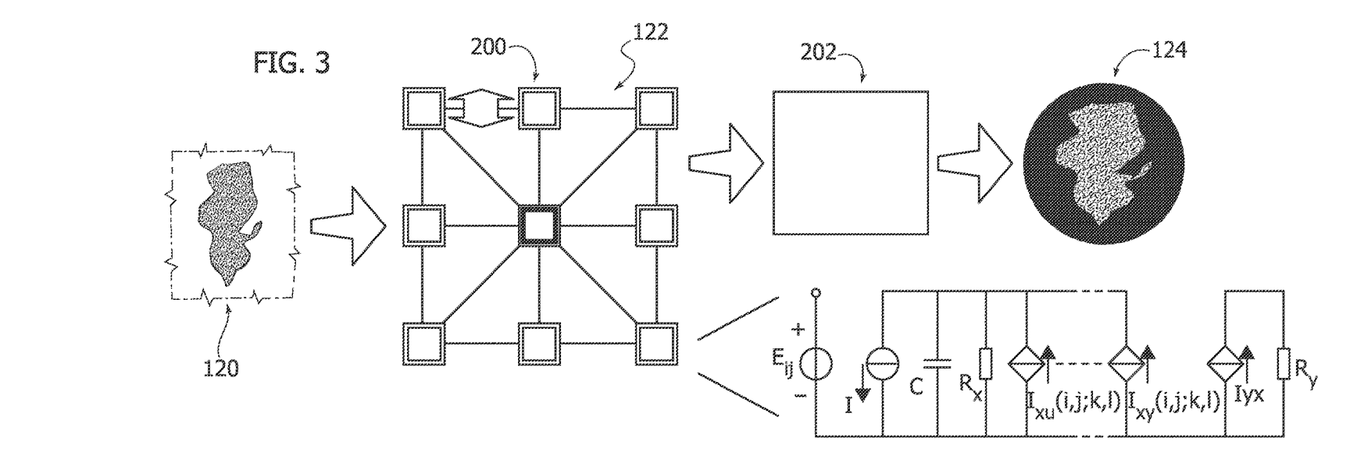
FIG. 3 is a block diagram exemplary of a possible implementation of embodiments.

In one or more embodiments, image segmentation with possible hair removal may involve operation as schematically represented in FIGS. 2 and 3, wherein the image 104 (if in color) may be converted to b/w (gray scale) 120.

For instance, in one or more embodiments, a conventional RGB to YCbCr transformation may be applied by extracting the luminance component "Y" which contains the gray-tone information on the nevus, and the chrominance component CbCr discarded insofar as this may not be useful for analysis as discussed in the following.

In one or more embodiments, the image 120 may be fed, e.g., in a step 122 to a cellular neural network (CNN) 200 (of a type known per se).

Cellular Neural Networks may provide a powerful and versatile system for real-time processing of images aimed at providing accurate and adaptive extraction of features in an input image.

In one or more embodiments a CNN 200 may be configured, e.g., as exemplified in the following, for segmenting an input image, e.g., by separating the foreground (e.g., a lesion L to be evaluated) from the background (e.g., skin, hair and other elements, providing no significant contribution to the evaluation).

In one or more embodiments an imaging mask (as schematically indicated at 202 in FIG. 3) may be applied for image segmentation.

Figure 4:
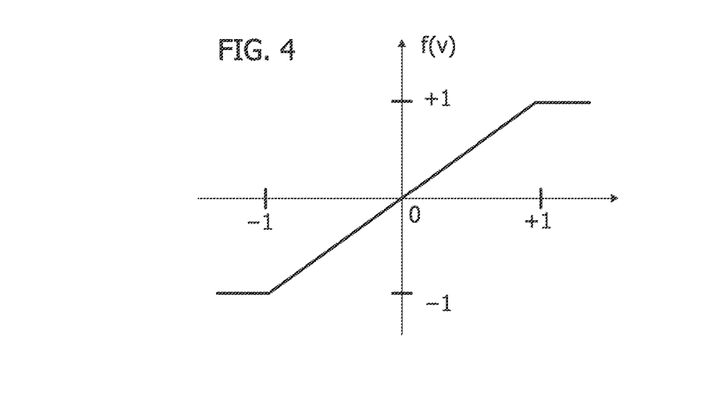
FIG. 4 is a diagram exemplary of possible details of implementation of embodiments.

FIG. 4 is exemplary of a characteristic which may be implemented in cells of the CNN 200 with an output f(v) (ordinate scale) and which is linearly dependent on input v (abscissa scale) for input values between −1 and +1, and is set (clamped) at −1 and +1 for input values v under −1 and above +1, respectively.

The function f(v) is exemplary of a PieceWise Linear (PWL) function for mapping the state of a single cell c(i,j) in the CNN 200 having a size corresponding to the size of the image "Y" discussed previously (e.g., the lesion L in a gray-tone scale). Each cell c(i,j) may have a state representative of a voltage $v_{xij}(t)$ at a capacitor C in the circuit exemplified in FIG. 3, which is an electrical circuit exemplary of the behaviour of an individual cell c(i,j) in the CNN 200.

For instance, when the image Y is fed to the CNN 200 (e.g., a pixel per cell), the input and the state of the CNN (that is, each individual cell therein) may represent the value of the image "Y" which will dictate the voltage $v_{xij}$ at the capacitor C. In one or more embodiments, the CNN 200 may process the image Y (e.g., according to templates A,B,I as exemplified in the following) in order to produce a certain state $v_{xij}(t)$ which may be re-mapped as an output, e.g., by means of the PWL function $f(v_{xij})$ as shown in FIG. 4.

Processing as exemplified in FIGS. 3 and 4 may be regarded as corresponding to generating a (segmented) pixel image p(x,y) of the lesion L (e.g., nevus) based on a relationship of the type:

$$v_{xij}(t) = v_{uij}(t) = p(x,y)$$

where $v_{xij}(t) = v_{uij}(t)$ with $v_{xij}(t)$ denoting the state of an individual cell set equal to the input $v_{uij}(t)$ in turn "loaded" with the image Y. In the circuit of the cell, these two voltages may represent the voltage across the capacitor C in the initial state.

$$C\frac{dv_{xij}(t)}{dt} = -\frac{1}{R_x}v_{xij}(t) + \sum_{C(k,l)\in Nr(i,j)} A(i,j;k,l)v_{ykl}(t) + \sum_{C(k,l)\in Nr(i,j)} B(i,j;k,l)v_{ukl}(t) + I$$

Processing in the CNN 200 as exemplified in FIGS. 3 and 4 may be represented, e.g., by means an integro-differential state equation for the CNN, e.g.:

$$A(i,j;k,l) = \begin{bmatrix} 0 & 0 & 0 \\ 0 & 0 & 0 \\ 0 & 0 & 0 \end{bmatrix}$$

$$B(i,j;k,l) = \begin{bmatrix} 3 & 0 & 3 \\ 0 & 3 & 0 \\ 3 & 0 & 0 \end{bmatrix}$$

$$I = 0.7$$

where (see, e.g., FIG. 3):

C=capacitance value of the capacitor C in a cell c(i,j)
$R_x$=resistance value of the resistor in a cell c(i,j)
$v_{ukl}(t)$=cell input voltage;
$v_{ykl}(t)$=cell output voltage;
$I_{xy}(i,j;k,l) = A(i,j;k,l)v_{ykl}$
$I_{xu}(i,j;k,l) = B(i,j;k,l)v_{ukl}$ with A and B representing a feedback template and control template, that is sets of values defining the type of image processing of the image Y performed in the CNN 200 (that is the values of the circuit parameters C, Rx, etc. . . . in the exemplary case of processing performed by hardware as a possible—at least partial—alternative to software), with $$v_{y,i,j}(t) = \frac{1}{2}(|v_{xij}(t)_{+1}| - |v_{xij}(t)_{-1}|)$$

where $I_{xy}$ and $I_{xu}$ denote the capacitor charge and source currents, respectively, in the cell circuit and with $$N_r(i,j) = C(k,l)$$

$$(\max(|k-i|, |l-j|) \le r,$$

$$1 \le k \le M, 1 \le l \le N)$$

where $N_r(i, j)$=identifies a so-called neighborhood of the cell, that is a set cells interacting during processing;

$C(k, l)$=identifies a single CNN cell belonging to the neighborhood;

r=is an amplitude radius which defines the neighborhood of a single cell (e.g., 3×3, 9×9, and so on).

Figure 5:
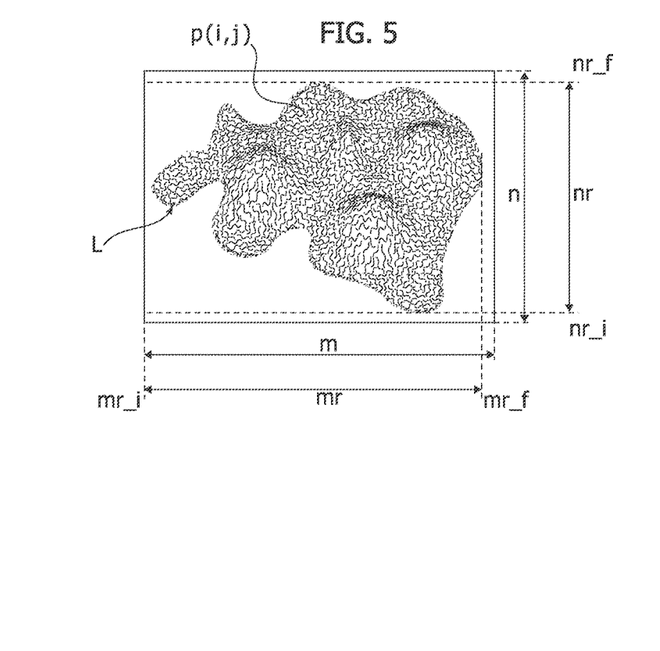
FIG. 5 is exemplary of certain parameters which may be used in image processing according to embodiments as exemplified herein.

In one or more embodiments, processing as discussed in the foregoing may result in a segmented image 124 of the lesion L (possibly with hair removed) which may be re-arranged (step 126) as schematically represented in FIG. 5, that is as an image including pixels p(i,j) extending over an, e.g., rectangular area of m×n pixels with the lesion L (for simplicity, a nevus will be steadily referred to hereinafter as an example) extending over a range mr (between mr_i and mr_f) along a first axis and over a range nr (between nr_i and nr_f) along a second axis orthogonal to the first axis.

It will otherwise be appreciated that operation of one or more embodiments may be largely unaffected by lesion (e.g., nevus) orientation with respect of those axes and/or the choice of the axes.

In one or more embodiments feature processing of the image 126 as exemplified by block 140 in FIG. 2 may involve computing a (first) set of values or "features" $F_1$ to $F_{12}$ according to the following formulas:

$$F_1 = \log\left(\frac{1}{m \cdot n} \sum_{i=mr_i}^{mr_f} \sum_{j=nr_i}^{nr_f} p(i,j)\right)$$

$$F_2 = \log\left(\frac{1}{mr \cdot nr} \sum_{i=1}^{m} \sum_{j=1}^{n} (|p(i,j) - F_1|)\right)$$

$$F_3 = \log\left(\frac{1}{mr \cdot nr} \sum_{i=1}^{m} \sum_{j=1}^{n} (p(i,j) - F_1)^2\right)$$

$$F_4 = \sqrt{|F_3|}$$

$$F_5 = \log\left(\frac{\pi}{2} \cdot \frac{1}{m \cdot n} \sum_{i=1}^{m} \sum_{j=1}^{n} (|p(i,j) - F_1|)\right)$$

$$F_6 = -\sum_i \sum_j (\Theta(p'(i,j)) \cdot \log(\Theta(p'(i,j)))$$

$$F_7 = \log\left(\sqrt{|F_3 - (F_6)^2|}\right)$$

$$F_8 = \log\left(\frac{1}{mr \cdot nr} \sum_{i=1}^{m} \sum_{j=1}^{n} \left(\frac{p(i,j) - F_1}{F_4}\right)^3\right)$$

$$F_9 = \log\left(\frac{1}{mr \cdot nr} \sum_{i=1}^{m} \sum_{j=1}^{n} \left(\left|i - \frac{m}{2}\right|\right) \cdot \left(\left|j - \frac{n}{2}\right|\right) \left(\frac{p(i,j) - F_1}{F_4}\right)^4\right)$$

$$F_{10} = \log\left(\frac{1}{mr \cdot nr} \sum_{i=1}^{m} \sum_{j=1}^{n} \left(\left|i - \frac{m}{2}\right|\right) \cdot \left(\left|j - \frac{n}{2}\right|\right) \left(\frac{p(i,j) - F_1}{F_4}\right)^5\right)$$

-continued $$F_{11} = \log\left(\frac{1}{mr \cdot nr} \sum_{i=1}^{m} \sum_{j=1}^{n} \left(\left|i - \frac{m}{2}\right|\right) \cdot \left(\left|j - \frac{n}{2}\right|\right) \left(\frac{p(i,j) - F_1}{F_4}\right)^6\right)$$

$$F_{12} = \log\left(\frac{1}{mr \cdot nr} \sum_{i=1}^{m} \sum_{j=1}^{n} \left(\left|i - \frac{m}{2}\right| \cdot \left|j - \frac{n}{2}\right| \cdot p(i,j)\right)\right)$$

It will be generally appreciated that "feature" $F_1$ may be regarded as indicative of an average value (in a log scale) of the pixel values p(i,j) while, e.g., features $F_2$, $F_3$, $F_8$, $F_9$, $F_{10}$ and $F_{11}$ may be regarded essentially as indicative of first order (average) and higher order (central) moments—cumulants, in view of the log scale—of the distribution of absolute (modulus) deviations of the pixel values with respect to the average value as represented by feature $F_1$.

Feature $F_4$ may be regarded essentially as providing a scaling/normalization factor.

Feature $F_5$ may be regarded essentially as corresponding to feature $F_2$, with summation weighted over the area m×n instead of mr×nr and including a weighing factor π/2.

Feature $F_6$ is intended to take into account the (spatial) frequency rate $\Theta(p'(i,j))$ of the image pixels.

Feature $F_7$ may be regarded essentially as providing a further scaling/normalization factor in view of features $F_3$ and $F_6$.

In brief, the first set of values or "features" considered in the foregoing may be regarded to be indicative—e.g., via the value or feature $F_{12}$—of the (central) moments—of the distribution of the pixels in the image of the lesion (e.g., nevus) which is evaluated.

In one or more embodiments, the feature designated $F_{12}$ may regarded as providing, e.g.:

a measure of melanocytes distribution of the skin epidermis;

a measure of nevus area/dermoscopy area ratio (fixed input dermo-image size);

a measure of nevus irregularities due to weighted average of pixels intensity;

a measure of nevus edges (borders);

a measure of pixels intensity distribution due to weighted average computation with specific weights at border parts of nevus.

In one or more embodiments, the feature designated $F_{12}$ may implement the A(Asymmetry), B(Borders), C(Color), D (Diameter) sub-rules as used by oncologists to identify a suspected skin lesion (the so called ABCDE method).

In one or more embodiments, the feature designated $F_{12}$:

may be space invariant, so that image registration may not be required during follow-up of nevus;

may be applied to gray intensity image only without information on colors.

As further discussed in the following (e.g., in connection with feature $F_{17}$) it was observed that features such as $F_8$ and $F_9$ may be helpful in providing an average measure of (custom average) skewness and kurtosis of the analyzed nevus.

In statistics:

skewness is a measure of the asymmetry of the probability distribution of a random value about its average (mean) value, kurtosis provides a measure of the "tailedness" of the probability distribution of a random value.

Both skewness and kurtosis thus describe the shape of a probability distribution.

In one or more embodiments, feature processing of the image 126 as exemplified by block 140 in FIG. 2 may also involve computing a (second) set of values or "features" $F_{13}$ to $F_{17}$ according to the following formulas:

$$F_{13} = \log\left(\frac{1}{mr \cdot nr}\sum_{i=1}^{m}\sum_{j=1}^{n}\left(\left|i-\frac{m}{2}\right| \cdot \left|j-\frac{n}{2}\right| \cdot (p(i,j))^2\right)\right)$$

$$F_{14} = \log\left(\frac{1}{mr \cdot nr}\sum_{i=1}^{m}\sum_{j=1}^{n}\left(\left|i-\frac{m}{2}\right| \cdot \left|j-\frac{n}{2}\right| \cdot (p(i,j) \cdot (i-j)^2)\right)\right)$$

$$F_{15} = \log\left(\frac{1}{mr \cdot nr}\sum_{i=1}^{m-k}\sum_{j=1}^{n-k}\left(\left|i-\frac{m}{2}\right| \cdot \left|j-\frac{n}{2}\right| \cdot (|p(i,j) - p(i+k, j+k)|)\right)\right)$$

$$F_{16} = \log\left(\frac{1}{mr \cdot nr}\sum_{i=1}^{m-k}\sum_{j=1}^{n-k}\left(\left|i-\frac{m}{2}\right| \cdot \left|j-\frac{n}{2}\right| \cdot \right.\right.$$

$$\left.\left.((p(i,j) - F_1) \cdot (p(i+k, j+k) - F_1))\right)\right)$$

$$F_{17} = \log\left(m \cdot n \cdot \frac{1}{6} \cdot \frac{1}{mr \cdot nr} \cdot \left((F_8)^2 + \left(\frac{1}{4} \cdot (F_9 - 3)^2\right)\right)\right)$$

In brief, the second set of values or "features" $F_{13}$ to $F_{17}$ considered in the foregoing may be regarded to be indicative—e.g., via the value or feature $F_{17}$—of the shape of the distribution of the pixels in the image of the lesion (e.g., nevus) which is evaluated.

In one or more embodiments, the feature designated $F_{17}$ may represent a "customized" representation of the Jarque-Bera (JB) equation used (e.g., in economics and statistics) to analyze a Gaussian distribution of samples showing specific skewness and kurtosis (the meaning of skewness and kurtosis has been discussed previously).

Resorting to the JB equation may offer one or more of the following advantages:

it may provide an average measure of custom average skewness (see e.g., feature $F_8$) and custom average kurtosis (see e. g. $F_9$) of the analyzed nevus;

the skewness and kurtosis ad used in the processing pipeline may be customized: moreover, the used kurtosis ($F_9$) may provide a weighted average measure of kurtosis pixels.

Also, the feature $F_{17}$ may provide one or more of the following:

a specific, accurate average measure of the asymmetry, border irregularity of the analyzed nevus ("A", "B", of the ABCDE rule);

a measure of nevus irregularities based on custom skewness and kurtosis of the analyzed nevus;

space invariability, that is no dependency on pixel orientation;

a specific indicator of nevus morphology suitable to discriminate with high accuracy benign skin lesions with respect to dysplastic ones;

a statistic model of the nevus which under specific hypothesis can be represented as random variable with Gaussian distribution of probability.

In one or more embodiments, feature processing of the image 126 may include edge detection at 142.

In one or more embodiments, edge detection may be implemented by using again a Cellular Neural Network (e.g., of the type exemplified previously as 200 in connection with segmentation of the lesion image) by adapting—in a manner known per se—the cloning/control templates so that the CNN may process the input image 120 of the lesion in order to extract the edges thereof.

It will be appreciated that, in one or more embodiments, this may occur by exploiting, at least partly, the same processing hardware used for image segmentation.

For instance, in one or more embodiments, edge detection CNN processing may be based on the following relationships:

$$C\frac{dv_{xij}(t)}{dt} = -\frac{1}{R_x}v_{xij}(t) +$$

$$\sum_{C(k,l)\in Nr(i,j)} A(i,j;k,l)v_{ykl}(t) + \sum_{C(k,l)\in Nr(i,j)} B(i,j;k,l)v_{ukl}(t) + I$$

with $$A(i,j;k,l) = \begin{bmatrix} 0 & 0 & 0 \\ 0 & 0 & 0 \\ 0 & 0 & 0 \end{bmatrix}$$

$$B(i,j;k,l) = \begin{bmatrix} -1 & -1 & -1 \\ -1 & 8 & -1 \\ -1 & -1 & -1 \end{bmatrix}$$

$$I = -1$$

where the various entities have the same meaning discussed previously, save for the values being dictated by the edge detection processing involved.

In one or more embodiments feature processing as exemplified by block 144 in FIG. 2 may involve computing a (third) set of values or "features" $F_{18}$ to $F_{22}$, respectively, according to the following formulas:

$$F_{18} = \log\left(\frac{1}{m \cdot n}\sum_{i=mr_i}^{mr_f}\sum_{j=nr_i}^{nr_f} p(i,j)\right)$$

$$F_{19} = \log\left(\pi \cdot \left(\frac{nr_f - nr_i}{2}\right)^2\right)$$

$$F_{20} = \log\left(2 \cdot \pi \cdot \left(\frac{nr_f - nr_i}{2}\right)\right)$$

$$F_{21} = \frac{\min(mr, nr)}{\max(mr, nr)}$$

$$F_{22} = \log$$

$$\left(\frac{1}{mr \cdot nr} \cdot \left(\sum_{i=1}^{round(\frac{m}{2})}\sum_{j=1}^{n}\left(\left|i-\frac{m}{2}\right| \cdot \left|j-\frac{n}{2}\right| \cdot \frac{|p(i,j) - p(i+1,j)|}{\sqrt{(p(i,j))^2 + (p(i+1,j))^2}}\right) + \right.\right.$$

$$\left.\left.\left(\sum_{i=1}^{m}\sum_{j=1}^{round(\frac{n}{2})}\left(\left|i-\frac{m}{2}\right| \cdot \left|j-\frac{n}{2}\right| \cdot \frac{|p(i,j) - p(i,j+1)|}{\sqrt{(p(i,j))^2 + (p(i,j+1))^2}}\right)\right)\right)\right)$$

where round(.) in feature $F_{22}$ indicates rounding (e.g., to the nearest higher integer).

The third set of values or "features" $F_{18}$ to $F_{22}$ considered in the foregoing may be regarded as additionally indicative of the shape of the distribution of the pixels in the image of the lesion (e.g., nevus) which is evaluated, e.g., with the value or feature $F_{22}$ providing, e.g.:

a specific adaptive ad-hoc weighted average measure of nevus asymmetry ("A" of the ABCDE rule) with specific weights for border part of nevus;

a specific weighted average measure of symmetry ratio between borders and nevus core;

a specific weighted measure of symmetry distribution of the near pixels of nevus segmented dermo-image;

a normalized specific weighted measure of nevus symmetry (which may be useful for follow-up checks as the measure of symmetry is normalized with respect to pixel intensity);

a specific weighted average measure of ratio between nevus symmetry and "gray-level power" represented by denominator of the proposed feature as color in the proposed pipeline replaced by gray intensity (which may provide an add-on to the classical ABCDE method by providing as we performs a further measure A/C, that is a ratio weighted measure between color power of nevus (gray intensity) with asymmetry as previously discussed;

a specific weighted measure of nevus symmetry as computed for each orientation: the first part of the equation performs a computation mainly along the y-axis while the second part operates mainly along the x-axis.

As discussed previously for the feature $F_{12}$, the feature $F_{22}$ is space invariant so that no specific issues of image registration may arise during follow-up.

In one or more embodiments, the specific computational details of steps 140, 142, 144 (and 160, as discussed in the following) may differ from those exemplified herein. Also, one or more embodiments may not necessarily involve calculation of all the features $F_1$ to $F_{22}$ exemplified herein (that is, in one or more embodiments, only a part of these features may be calculated).

In one or more embodiments, fuzzy-like, if-then-else evaluation at 160 may involve computing a total feature score $F_{tot}$ for the features calculated, e.g., as:

$$F_{tot} = \frac{1}{N_F} \sum_{k=1}^{N_f} F_k; N_F = 22$$

with such a score and the values/features $F_{12}$, $F_{17}$ and $F_{22}$ compared with a set of thresholds $Th_{malignant}$, $Th_{central-moment}$, $Th_{cosine}$, and $Th_{Jarque-Bera}$ which may be defined, e.g., experimentally, as:

$Th_{malignant} = 17.50$
$Th_{central-moment} = 10$
$Th_{cosine} = 5$
$Th_{Jarque-Bera} = 80$ with if-then-else evaluation performed, e.g., based on the criteria as expressed in the pseudo-code reproduced below:

```
if (F_tot ≥ Th_malignant) {
    if ((F_12 ≥ Th_central-moment)&&(F_22 ≥ Th_cosine)){
        if (F_17 ≥ Th_Jarque-Bera)
            Very High Risk: P(Melanoma) = ~100 %. Needed Nevus biopsy.
        else
            High Risk: P(Melanoma) = 90 - 100 %. Needed Nevus biopsy.
    }
    if ((F_12 < Th_central-moment)&&(F22 < Th_cosine)){
        if (F_17 < Th_Jarque-Bera)
            Very Low Risk: P(Melanoma) < 1 %. Benign nevus . No Follow-up
        else
            Low Risk: P(Melanoma) = 1..5 %. Benign nevus. No Follow-up
    }
    if ((F_12 < Th_central-moment)||(F_22 < Th_cosine)){
        if (F_17 < Th_Jarque-Bera)
            Medium Risk: P(Melanoma) = 30 - 40 %. 3-month Follow-up.
        else
            Medium Risk+: P(Melanoma) = 45 - 60 %. 2-month Follow-up
    }
if (F_tot < Th_malignant) {
    if ((F_12 ≥ Th_central-moment)&&(F_22 ≥ Th_cosine)){
        if(F_17 ≥ Th_Jarque-Bera)
            Medium Risk+: P(Melanoma) = 45 - 60 %. 2-month Follow-up
        else
            Medium Risk: P(Melanoma) = 30 - 40 %. 3-month Follow-up.
    }
    if ((F_12 < Th_central-moment)&&(F_22 < Th_cosine)){
        if (F_17 < Th_Jarque-Bera)
            Very Low Risk: P(Melanoma) = < 1 %. Benign nevus
        else
            Low Risk: P(Melanoma) = 1 - 5 %. Benign Nevus. No Follow-up
    }
    if ((F_12 < Th_central-moment)||(F_22 < Th_cosine)){
        if (F_17 < Th_Jarque-Bera)
            Low Risk: P(Melanoma) = 1 - 5 %. Benign Nevus. No Follow-up
        else
            Medium Risk: P(Melanoma) = 30 - 40 %. 3-month Follow-up
    }
}
```

In one or more embodiments the outcome of comparison of the total feature score $F_{tot}$ with $Th_{malignant}$ may discriminate between an area of high-medium expected risk ($F_{tot} \geq Th_{malignant}$) and an area of medium-low expected risk ($F_{tot} < Th_{malignant}$), while comparisons of features $F_{12}$, $F_{22}$ and $F_{17}$ with $TH_{central-moment}$, $Th_{cosine}$ and $Th_{Jarque-Bera}$ as exemplified above may permit to "refine" evaluation within each area.

By way of recap of the previous discussion, the definitions of the discrimination features $F_{12}$, $F_{22}$ and $F_{17}$ are reported below:

$$F_{12} = \log\left(\frac{1}{mr \cdot nr}\sum_{i=1}^{m}\sum_{j=1}^{n}\left(\left|i-\frac{m}{2}\right| \cdot \left|j-\frac{n}{2}\right| \cdot p(i,j)\right)\right)$$

$$F_{22} = \log$$

$$\left(\frac{1}{mr \cdot nr} \cdot \left(\sum_{i=1}^{round\left(\frac{m}{2}\right)}\sum_{j=1}^{n}\left(\left|i-\frac{m}{2}\right| \cdot \left|j-\frac{n}{2}\right| \cdot \frac{|p(i,j)-p(i+1,j)|}{\sqrt{(p(i,j))^2+(p(i+1,j))^2}}\right)\right) + \right.$$

$$\left. \left(\sum_{i=1}^{m}\sum_{j=1}^{round\left(\frac{n}{2}\right)}\left(\left|i-\frac{m}{2}\right| \cdot \left|j-\frac{n}{2}\right| \cdot \frac{|p(i,j)-p(i,j+1)|}{\sqrt{(p(i,j))^2+(p(i,j+1))^2}}\right)\right)\right)$$

$$F_{17} = \log\left(m \cdot n \cdot \frac{1}{6} \cdot \frac{1}{mr \cdot nr} \cdot \left((F_8)^2 + \left(\frac{1}{4} \cdot (F_9-3)^2\right)\right)\right)$$

with features $F_8, F_9, F_1, F_3$ and $F_4$ included in the definition of feature $F_{17}$ defined as:

$$F_8 = \log\left(\frac{1}{mr \cdot nr}\sum_{i=1}^{m}\sum_{j=1}^{n}\left(\frac{p(i,j)-F_1}{F_4}\right)^3\right)$$

$$F_9 = \log\left(\frac{1}{mr \cdot nr}\sum_{i=1}^{m}\sum_{j=1}^{n}\left(\left|i-\frac{m}{2}\right|\right) \cdot \left(\left|j-\frac{n}{2}\right|\right)\left(\frac{p(i,j)-F_1}{F_4}\right)^4\right)$$

$$F_1 = \log\left(\frac{1}{m \cdot n}\sum_{i=mr_i}^{mr_f}\sum_{j=nr_i}^{nr_f}p(i,j)\right)$$

$$F_3 = \log\left(\frac{1}{mr \cdot nr}\sum_{i=1}^{m}\sum_{j=1}^{n}(p(i,j)-F_1)^2\right)$$

$$F_4 = \sqrt{|F_3|}$$

In one or more embodiments, the feature designated $F_{12}$ may provide one or more of the following advantages:

it may provide a specific measure of Asymmetry/Borders/Diameter and color distribution of the nevus (ABCD rule), which may improve over conventional methods documents in the literature as it uses a weighted average measure with specific weighting to borders of nevus;

it may provide a measure of ABCD information without issues related to a gray-level co-occurrence matrix generally used by classical algorithms proposed in the literature to compute image features/textures;

low complexity of computation involved;

invariance with respect to orientation, while conventional methods may need to compute a gray level co-occurrence matrix for plural pixel pair orientations, e.g., 0°, 45°, 90°, 135°; $F_{12}$ being invariant with respect orientation avoids having to perform $F_{12}$ computation for plural orientations of pixel pairs;

distance issues are overcome: as noted above, in conventional methods a gray level co-occurrence matrix may need be computed for plural pixel pairs at distances 5, 10, 15, 20, 30, . . . ; $F_{12}$ being invariant makes it possible to avoid multiple computations with different pixel pair distances.

In one or more embodiments, the feature designated $F_{17}$ may provide one or more of the following advantages:

a feed-forward feature, easy follow-up usage, only gray-level image needed;

low complexity feature which may dispense with learning, training, clustering hypothesis (e.g., SVM/K-mean), thus avoiding fitting issues or problems related to network topology;

high accuracy, specificity and sensitivity;

space and orientation invariability, thus avoiding computations for different pixel pair orientations or distances as required for conventional features/textures (gray-level co-occurrence);

a specific measure of asymmetry and border irregularities of nevus is provided based on skewness and kurtosis as well as on weighted average distribution of melanocytes over the nevus (see e.g., $F_3$, $F_4$, $F_8$), with improved accuracy with respect to gray-level textures.

In one or more embodiments, the feature designated $F_{22}$ may provide one or more of the following advantages:

it may provide an ad-hoc weighted and customized measure of asymmetry nevus ("A" part of ABCDE rule), an important feature used by oncologist to discriminate nevus;

it may provide a new rule for discriminating nevus i.e. the so called A/C rule i.e. a ratio weighted measure between color power of nevus (gray intensity) with asymmetry;

no image registration required for follow-up; follow-up is simple and efficient;

improved specificity and sensitivity and accuracy issues in comparison with classical methods based on, e.g., gray-level co-occurence matrix, SVM/K-mean, artificial neural networks with issues of over-fitting, learning/training, clusters selections;

high sensitivity and specificity as provided, e.g., by specific asymmetry measure calibrated to morphology of analyzed nevus;

low computational complexity;

feed-forward feature;

applicability to gray-level images obtained from original color dermoscopy (e.g., RGB image), with ensuing simplicity in comparison with classical methods as applied to color dermoscopy, e.g., for each color plane.

One or more embodiments may thus perform "all-in-one":

nevus segmentation from dermoscopy (also in the presence of hair), with segmentation performed, e.g., by Cellular Neural Network (CNN) layer configured to perform real-time nevus segmentation and hair removing, without any learning phase required;

nevus analysis with ad-hoc customized subset of mathematical and morpho-geometric features;

fuzzy-like operation based on if-then-else rules and combining results of previous subsets of features, with the capability of providing nevus classification with associated probability of malignant evolution and follow-up rate.

Use of the method and system of one or more embodiments may be detected, e.g., by selectively forcing small changes (e.g., $\varepsilon_1$, $\varepsilon_2$, $\varepsilon'$, $\varepsilon''$) in those lesion parameters which come into play in defining features such as $F_{12}$, $F_{22}$, $F_{17}$ and noting the corresponding changes resulting in the output O from the evaluation process at 160.

One of more embodiments may thus provide a method of analyzing digital (dermoscopic) images (e.g., 104) of skin lesions (L), such as, e.g., nevus images, in support of diagnosis to be provided by a physician, with the images including pixels distributed over a lesion area (see e.g., the m×n area in FIG. 5, with the lesion covering a range mr×nr), the method including processing (see e.g., 120, 122, 140, 142, 144) pixels in an analyzed image by:

i) calculating:
a first set of values (e.g., "features" $F_1, \ldots, F_{12}$) indicative of—e.g., (central) moments of—the distribution of the image pixels, wherein the first set of values includes a first discrimination value (e.g., $F_{12}$) indicative of a weighted average of the image pixels with weighing at the border of the lesion, a second set of values (e.g., "features" $F_{13} \ldots, F_{17}$) indicative of the shape of the lesion, wherein the second set of values includes a second discrimination value (e.g., $F_{17}$) indicative of skewness and kurtosis of the distribution of the image pixels, and a third set of values (e.g., "features" $F_{18} \ldots, F_{22}$) indicative of symmetry of the lesion wherein the third set of values includes a third discrimination value (e.g., $F_{22}$) indicative of the ratio of symmetry and gray-level power of the distribution of the image pixels, ii) providing a total additive score of the values in the sets of values—see e.g., the sum $$F_{tot} = \frac{1}{N_F} \sum_{k=1}^{N_f} F_k; N_F = 22$$

iii) comparing:
the total additive score with a total score threshold (e.g., $Th_{malignant}$),
the first ($F_{12}$), second ($F_{17}$) and third ($F_{22}$) discrimination values with respective first, second and third discrimination threshold values (e.g., $Th_{central-moment}$, $Th_{Jarque-Bera}$, $Th_{cosine}$), iv) providing an output classification (e.g., O) for the image analyzed as a function of the results of comparing the total additive score with a total score threshold and comparing the first ($F_{12}$), second ($F_{17}$) and third ($F_{22}$) discrimination values with respective first, second and third discrimination threshold values.

One of more embodiments may include applying edge detection (e.g., 142) to the analyzed image before calculating (e.g., 144) the third set of values.

One of more embodiments may include converting the analyzed image to gray scale (e.g., 104>120 in FIG. 2) before calculating the sets of values (in one more embodiments, gray scale values may be calculated only when needed).

One of more embodiments may include calculating the second discrimination value ($F_{17}$) as a Jarque-Bera equation indicative of skewness and kurtosis of the distribution of the image pixels.

One of more embodiments may include applying to the analyzed image (e.g., 120) segmentation, optionally with hair removal.

In one or more embodiments the segmentation and/or edge detection may include cellular neural network (e.g., 200, 202) processing of the image.

One of more embodiments may provide a system for analyzing digital images of skin lesions, the images including pixels distributed over a lesion area, the system including processing circuits configured (e.g., as f/w and/or s/w) for processing the pixels of an analyzed image by:

i) calculating:
a first set of values indicative of (e.g., moments of) the distribution of the image pixels, wherein the first set of values includes a first discrimination value ($F_{12}$) indicative of a weighted average of the image pixels with weighing at the border of the lesion, a second set of values indicative of the shape of the lesion, wherein the second set of values includes a second discrimination value ($F_{17}$) indicative of skewness and kurtosis of the distribution of the image pixels, and a third set of values indicative of symmetry of the lesion wherein the third set of values includes a third discrimination value ($F_{22}$) indicative of the ratio of symmetry and gray-level power of the distribution of the image pixels, ii) providing a total additive score of the values in the sets of values, iii) comparing:
the total additive score with a total score threshold,
the first, second and third discrimination values with respective first, second and third discrimination threshold values, and iv) providing an output classification (O) for the image analyzed as a function of the results of comparing the total additive score with a total score threshold and comparing the first, second and third discrimination values with respective first, second and third discrimination threshold values, the system being configured for operating according to the method of one of more embodiments.

One of more embodiments may include at least one cellular neural network circuit for applying segmentation and/or edge detection to the analyzed images.

One of more embodiments may include a dermoscopy instrument (e.g., D) including a system according to one of more embodiments, optionally in combination with a dermoscopic camera (e.g., C) to provide digital images of skin lesions to be analyzed.

One of more embodiments may include a computer program product loadable the memory of at least one computer (e.g., a DSP) and including software code portions for executing the steps of the method of one of more embodiments when the product is run on at least one computer.

Without prejudice to the underlying principles, the details and embodiments may vary, even significantly, with respect to what has been described in the foregoing by way of example only, without departing from the extent of protection.

The extent of protection is determined by the claims that follow.

What is claimed is:
1. A method of analyzing digital images of skin lesions, the images including pixels distributed over a lesion area, the method including using at least one processor to process pixels in an analyzed image by:
calculating a first set of values indicative of a distribution of the image pixels, wherein the first set of values includes a first discrimination value indicative of a weighted average of the image pixels with weighing at a border of the lesion;
calculating a second set of values indicative of lesion shape, wherein the second set of values includes a second discrimination value indicative of skewness and kurtosis of the distribution of the image pixels;
calculating a third set of values indicative of lesion symmetry, wherein the third set of values includes a third discrimination value indicative of a ratio of symmetry and gray-level power of the distribution of the image pixels;

providing a total additive score of the values in the first, second and third sets of values;

comparing the total additive score with a total score threshold;

comparing the first, second and third discrimination values with respective first, second and third discrimination threshold values; and providing an output classification for the image analyzed as a function of results of comparing the total additive score with the total score threshold and comparing the first, second and third discrimination values with respective first, second and third discrimination threshold values.

2. The method of claim 1, further comprising applying edge detection to the analyzed image before calculating the third set of values.

3. The method of claim 2, wherein applying the edge detection comprises cellular neural network processing of the analyzed image.

4. The method of claim 1, further comprising converting the analyzed image to gray scale before calculating the first, second and third sets of values.

5. The method of claim 1, wherein the second discrimination value is calculated as a Jarque-Bera equation indicative of skewness and kurtosis of the distribution of the image pixels.

6. The method of claim 1, further comprising applying segmentation to the analyzed image.

7. The method of claim 6, further comprising removing an image feature before calculating the first, second and third sets of values.

8. The method of claim 7, wherein removing the image feature comprises removing a feature related to hair.

9. The method of claim 6, wherein the segmentation comprises cellular neural network processing of the analyzed image.

10. A system for analyzing digital images of skin lesions, the images including pixels distributed over a lesion area, the system comprising:

processing circuits configured for processing the pixels of an analyzed image; and a non-transitory storage medium including software code for execution by the processing circuits, the software code including instructions for implementing a method comprising:

calculating a first set of values indicative of a distribution of the image pixels, wherein the first set of values includes a first discrimination value indicative of a weighted average of the image pixels with weighing at a border of the lesion;

calculating a second set of values indicative of lesion shape, wherein the second set of values includes a second discrimination value indicative of skewness and kurtosis of the distribution of the image pixels;

calculating a third set of values indicative of lesion symmetry, wherein the third set of values includes a third discrimination value indicative of a ratio of symmetry and gray-level power of the distribution of the image pixels;

providing a total additive score of the values in the first, second and third sets of values;

comparing the total additive score with a total score threshold;

comparing the first, second and third discrimination values with respective first, second and third discrimination threshold values; and providing an output classification for the image analyzed as a function of results of comparing the total additive score with the total score threshold and comparing the first, second and third discrimination values with respective first, second and third discrimination threshold values.

11. The system of claim 10, comprising a cellular neural network circuit for applying segmentation to the images.

12. The system of claim 10, comprising a cellular neural network circuit for applying edge detection to the images.

13. The system of claim 10, wherein the method further comprises converting the analyzed image to gray scale before calculating the first, second and third sets of values.

14. The system of claim 10, wherein the second discrimination value is calculated as a Jarque-Bera equation indicative of skewness and kurtosis of the distribution of the image pixels.

15. The system of claim 10, wherein the method further comprises applying segmentation to the analyzed image and removing an image feature before calculating the first, second and third sets of values.

16. A dermoscopy instrument comprising:

a dermoscopic camera to provide digital images of skin lesions to be analyzed; and processing circuits coupled to the dermoscopic camera and configured for processing pixels of the digital images using a method comprising:

calculating a first set of values indicative of a distribution of the image pixels, wherein the first set of values includes a first discrimination value indicative of a weighted average of the image pixels with weighing at a border of the lesion;

calculating a second set of values indicative of lesion shape, wherein the second set of values includes a second discrimination value indicative of skewness and kurtosis of the distribution of the image pixels;

calculating a third set of values indicative of lesion symmetry, wherein the third set of values includes a third discrimination value indicative of a ratio of symmetry and gray-level power of the distribution of the image pixels;

providing a total additive score of the values in first, second and third sets of values;

comparing the total additive score with a total score threshold;

comparing the first, second and third discrimination values with respective first, second and third discrimination threshold values; and providing an output classification for the image analyzed as a function of results of comparing the total additive score with the total score threshold and comparing the first, second and third discrimination values with respective first, second and third discrimination threshold values.

17. The dermoscopy instrument of claim 16, further comprising a non-transitory memory coupled to the processing circuits, the memory storing a computer program product that includes software code for executing the method.

18. The dermoscopy instrument of claim 16, comprising a cellular neural network circuit for applying segmentation to the images.

19. The dermoscopy instrument of claim 16, comprising a cellular neural network circuit for applying edge detection to the images.

20. The dermoscopy instrument of claim 16, wherein the method further comprises converting the digital image to gray scale before calculating the first, second and third sets of values.

* * * * *